United States Patent
Jang et al.

(10) Patent No.: US 12,137,710 B2
(45) Date of Patent: Nov. 12, 2024

(54) **FOOD COMPOSITION, FOR ALLEVIATING DIABETES, COMPRISING *Schisandra chinensis* FRUIT JUICE AND BEAN JUICE AND PREPARATION METHOD THEREOF**

(71) Applicant: KOREA FOOD RESEARCH INSTITUTE, Jeollabuk-do (KR)

(72) Inventors: Dai Ja Jang, Gyeonggi-do (KR); Hye Jeong Yang, Gyeonggi-do (KR); Min Jung Kim, Seoul (KR); Yu Jin Kim, Jeollabuk-do (KR)

(73) Assignee: KOREA FOOD RESEARCH INSTITUTE, Jeollabuk-do (KR)

( * ) Notice: Subject to any disclaimer, the term of this patent is extended or adjusted under 35 U.S.C. 154(b) by 258 days.

(21) Appl. No.: 17/423,571

(22) PCT Filed: Nov. 13, 2019

(86) PCT No.: PCT/KR2019/015479
§ 371 (c)(1),
(2) Date: Jul. 16, 2021

(87) PCT Pub. No.: WO2020/149506
PCT Pub. Date: Jul. 23, 2020

(65) Prior Publication Data
US 2022/0117275 A1    Apr. 21, 2022

(30) Foreign Application Priority Data
Jan. 17, 2019  (KR) .................. 10-2019-0006086

(51) Int. Cl.
| | |
|---|---|
| *A61K 36/79* | (2006.01) |
| *A23L 2/02* | (2006.01) |
| *A23L 11/65* | (2021.01) |
| *A23L 19/00* | (2016.01) |
| *A23L 33/105* | (2016.01) |
| *A61P 3/10* | (2006.01) |

(52) U.S. Cl.
CPC .............. *A23L 11/65* (2021.01); *A23L 2/02* (2013.01); *A23L 19/01* (2016.08); *A23L 33/105* (2016.08); *A61K 36/79* (2013.01); *A61P 3/10* (2018.01)

(58) Field of Classification Search
None
See application file for complete search history.

(56) References Cited

U.S. PATENT DOCUMENTS

| | | |
|---|---|---|
| 6,451,355 B1 | 9/2002 | Reisner |
| 2008/0233220 A1 | 9/2008 | Zhong |

FOREIGN PATENT DOCUMENTS

| | | | |
|---|---|---|---|
| KR | 1019980054257 | | 9/1998 |
| KR | 100417287 | | 1/2004 |
| KR | 100443022 | | 7/2004 |
| KR | 100457690 | | 11/2004 |
| KR | 100464815 | | 12/2004 |
| KR | 1020090036981 | | 4/2009 |
| KR | 20110096336 A | * | 8/2011 |
| KR | 101106200 | | 1/2012 |
| KR | 20120029585 | | 3/2012 |
| KR | 101156002 | | 6/2012 |
| KR | 101706019 | | 2/2017 |
| KR | 101706019 B1 | * | 2/2017 |
| KR | 1020170024877 | | 3/2017 |
| KR | 1020180065991 | | 6/2018 |
| WO | 200160386 | | 8/2001 |

OTHER PUBLICATIONS

Kang (KR 100871568—English translation—Dec. 2008).*
Grover, J.K., et al., "Anti-hyperglycemic effect of Eugenia jambolana and Tinospora cordifolia in experimental diabetes and their effects on key metabolic enzymes involved in carbohydrate metabolism," Journal of Ethnopharmacology 73 (2000) 461-470.

* cited by examiner

*Primary Examiner* — Susan Hoffman
(74) *Attorney, Agent, or Firm* — DUANE MORRIS LLP; Gregory M. Lefkowitz; Brandon A. Chan

(57) ABSTRACT

The present invention, which is a food composition for alleviating diabetes that contains *Schisandra chinensis* fruit water and bean juice as active ingredients, has a high inhibitory activity against α-glucosidase and prevents a rise of the blood sugar after meals, thereby alleviating diabetes. The food composition for alleviating diabetes can be prepared in different forms, such as soy milk, powdered soy milk, other forms of soy milk, or processed bean curd, and used in the preparation of health functional foods for blood sugar control or foods for diabetics according to the Special Purpose Foods of the general foods. In addition, the food composition for alleviating diabetes according to the present invention, when further containing a saccharified material of grain, maintains viscosity similar to that of regular soy milk by preventing agglomeration of the liquid soy milk and improves sensory properties, so it can be suitable for use in beverages such as soy milk or other forms of soy milk.

4 Claims, 1 Drawing Sheet

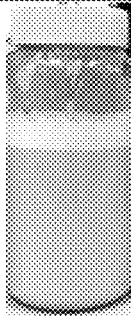

FOOD COMPOSITION, FOR ALLEVIATING DIABETES, COMPRISING Schisandra chinensis FRUIT JUICE AND BEAN JUICE AND PREPARATION METHOD THEREOF

CROSS-REFERENCE TO RELATED APPLICATIONS

This application is a § 371 national stage entry of International Application No. PCT/KR2019/015479, filed on Nov. 13, 2019, which claims priority to Korean Patent Application No. 10-2019-0006086, filed on Jan. 17, 2019, the entire contents of which are incorporated herein by reference.

TECHNICAL FIELD

The present invention relates to a food composition for alleviating diabetes that contains a mixture of *Schisandra chinensis* fruit water (Omisu) and bean juice as an active ingredient, and a preparation method thereof.

BACKGROUND ART

Diabetes refers to a condition in which insulin, a glucose-regulating hormone secreted from the β-cells of the pancreas, is insufficient or does not work properly, only to make the sugar build up in the blood rather than used as a fuel for energy, resulting in high blood sugar and the presence of sugar in the urine.

Diabetes is usually divided into insulin-dependent diabetes (type I diabetes) and insulin-independent diabetes (type II diabetes). Insulin-dependent diabetes occurs when insulin secretion is impaired with the pancreatic β-cells destroyed due to virus infection. It is also called juvenile-onset diabetes because it often develops in teens or young adults (in 20s). The condition is named as "insulin-dependent" because there is a risk of not maintaining life without insulin supplied from outside. Insulin-independent diabetes occurs when the pancreatic β-cells still produce insulin, but not enough to function properly due to obesity or the like. It is prevalent in adults more than 30 years old and thus also called adult-onset diabetes. The condition is named as "insulin-independent" because it is not necessity to supply insulin from outside in order to maintain life. Even so, this does not mean that insulin is not required for the treatment of hyperglycermia.

Diabetes treatment uses biguanides, thiazolidinedione, sulfonylurea, benzoic acid derivatives, and α-glucosidase inhibitors. Yet, the use of these drugs for diabetes has many side effects, so the World Health Organization (WHO) strongly recommends the use of natural products with few side effects for diabetes (Grover J K, Vats. V., Rathi. S S, *Journal of Ethnopharmacology*, 73, pp 461-470, 2000).

The natural products suggested to be effective in the treatment of diabetes may include, for example, a moxibustion extract (Korean Patent No. 464815), an anflamic acid derivative compound isolated from *Xanthomonas* obliquus (Korean Patent No. 457690), an extract of *Hovenia dulcis* (Korean Patent No. 417287), polysaccharides isolated from Angelicagigas (International Publication No. 2001-60386), and bile of Ruminant (U.S. Pat. No. 6,451,355).

On the other hand, α-glucosidase is a type of glycolytic enzyme present in the mucous membrane of the small intestine. The inhibition of α-glucosidase prevents the digestion of carbohydrates, delaying the absorption of sugar in the small intestine and thus preventing an abrupt increase in the blood glucose after meals.

Typical α-glucosidase inhibitors are Acarbose and Voglibose, which are commercially available. Yet, a long-term use of these inhibitors can lead to severe side effects, such as vomiting, diarrhea, and abdominal distension. Hence, there is a need for research on natural materials as a substitute for the α-glucosidase inhibitors that are safer and more excellent in the anti-hyperglycemic effect after meals than the inhibitors.

Omigalsu using *Schisandra chinensis* fruits (Omija), a Korean traditional beverage made of *Schisandra chinensis* fruits, soybeans and mungbeans, is prepared by soaking *Schisandra chinensis* fruits used as a main ingredient in water to obtain a *Schisandra chinensis* fruit juice and boiling the *Schisandra chinensis* fruit juice in combination with soybean juice or mungbean juice, adding some honey, and boiling the mixture again. The Omigalsu is kept refrigerated and consumed in cold or hot water. It has long been said that the Omigalsu helps quench thirst

PRIOR ART DOCUMENTS

Patent Documents (Patent Document 1) Korean Patent No. 464815
(Patent Document 2) Korean Patent Laid-Open Publication No. 2017-0024877

SUMMARY OF THE DISCLOSURE

It is an object of the present invention to provide a food composition for alleviating diabetes that contains a *Schisandra chinensis* fruit water (Omisu) and a bean juice as active ingredients.

It is another object of the present invention to provide a method for preparing the food composition for alleviating diabetes.

It is further another object of the present invention to provide the use of a complex of *Schisandra chinensis* fruit water and bean juice for preparation of a medicine for blood sugar control or diabetes treatment.

It is still further another object of the present invention to provide a treatment method for blood sugar control disorder or diabetes that includes administering a complex of *Schisandra chinensis* fruit water and bean juice to a patient with blood sugar control disorder or diabetes.

The food composition for alleviating diabetes according to the present invention for achieving the first object of the present invention may contain a *Schisandra chinensis* fruit water (Omisu) and a bean juice as active ingredients.

The food composition for alleviating diabetes may be a health functional food for blood sugar control or a food for diabetics.

Further, the food composition for alleviating diabetes may be soy milk, powdered soy milk, other forms of soy milk, or processed bean curd.

The *Schisandra chinensis* fruit water may be a *Schisandra chinensis* fruit juice or a *Schisandra chinensis* fruit extract.

The *Schisandra chinensis* fruit extract may be an extract of *Schisandra chinensis* fruits in water, alcohol, or a mixed solvent thereof.

The bean juice may be a liquid soy milk containing at least 7 wt. % of soybean solids extracted from soybeans.

The food composition for alleviating diabetes may include the *Schisandra chinensis* fruit water and the bean juice mixed at a weight ratio of 1:0.1~3, preferably 1:0.8~2.

The food composition for alleviating diabetes may further include a saccharified material of grain.

The saccharified material of grain may be prepared by saccharifying at least one grain selected from rice, wheat, and barley.

Further, the saccharified material of grain may be a powder prepared by mixing the grain with malt or a saccharifying enzyme to saccharify the grain and then drying the saccharified grain.

The food composition for alleviating diabetes may include the *Schisandra chinensis* fruit water, the bean juice, and the saccharified material of grain mixed at a weight ratio of 1:0.8~2:0.2~1.5.

The food composition for alleviating diabetes may further include at least one sweetener selected from the group consisting of aspartame, acesulfame calcium, sorbitol, trehalose, palatinose, tagatose, xylitol, and oligosaccharide.

In addition, the method for preparing a food composition for alleviating diabetes in order to achieve the second object of the present invention may include: (1) extracting juice from *Schisandra chinensis* fruit or obtaining an extract of *Schisandra chinensis* fruit in water, alcohol, or a mixed solvent thereof to prepare a *Schisandra chinensis* fruit water; (2) steaming and grinding beans and then filtering out bean pulps to obtain a bean juice with bean pulps removed; and (3) mixing the *Schisandra chinensis* fruit water and the bean juice.

The method for preparing a food composition for alleviating diabetes may further include mixing a grain with malt or a saccharifying enzyme to saccharify the grain and then drying the saccharified grain to obtain a saccharified material of grain.

The present invention is also directed to the use of a complex of a *Schisandra chinensis* fruit water and a bean juice for preparation of a medicine for blood sugar control or diabetes treatment, where the *Schisandra chinensis* fruit water is a *Schisandra chinensis* fruit juice or a *Schisandra chinensis* fruit extract, and the *Schisandra chinensis* fruit extract is an extract in water, alcohol, or a mixed solvent thereof.

The present invention is also directed to a treatment method for blood sugar control disorder or diabetes that includes administering a complex of a *Schisandra chinensis* fruit water and a bean juice to a patient with blood sugar control disorder or diabetes, where the *Schisandra chinensis* fruit water is a *Schisandra chinensis* fruit juice or a *Schisandra chinensis* fruit extract, and the *Schisandra chinensis* fruit extract is an extract in water, alcohol, or a mixed solvent thereof.

Containing a mixture of *Schisandra chinensis* fruit water and bean juice as an active ingredient, the food composition for alleviating diabetes according to the present invention has a high inhibitory activity against α-glucosidase and inhibits a rise of the blood glucose after meals, thereby alleviating diabetes. The food composition for alleviating diabetes may be prepared into different forms, such as soy milk, powdered soy milk, other forms of soy milk, or processed bean curd, and used in the preparation of health functional foods for blood sugar control or foods for diabetics according to the Special Purpose Foods of the general foods.

In addition, the food composition for alleviating diabetes according to the present invention, if further containing a saccharified material of grain, maintains viscosity similar to that of regular soy milk by preventing agglomeration of the liquid soy milk and improves sensory properties, so it can be suitable for use in beverages such as soy milk or other forms of soy milk.

BRIEF DESCRIPTION OF THE DRAWINGS

FIG. 1 shows whether or not the food compositions for alleviating diabetes according to Examples 1, 8, 9, 10, and 11 coagulate immediately after preparation and in 30 minutes and 2 hours after preparation in Experimental Example 1.

DETAILED DESCRIPTION OF THE DISCLOSURE

The present invention is directed to a food composition for alleviating diabetes that contains *Schisandra chinensis* fruit water (Omisu) and bean juice as active ingredients, and a preparation method thereof.

The conventional Omigalsu is prepared using *Schisandra chinensis* fruits, mung bean juice, and honey (or sugar) and used to quench thirst, but it has no efficacy to improve diabetes. The present invention, in contrast, has been proven to be effective in alleviating diabetes.

Hereinafter, the present invention will be described in further detail.

The food composition for alleviating diabetes according to the present invention contains a *Schisandra chinensis* fruit water (Omisu) and a bean juice as active ingredients.

The food composition for alleviating diabetes has a high inhibitory activity against α-glucosidase and inhibits a rise of the blood glucose after meals, so it can be used as a health functional food for blood sugar control.

The food composition for alleviating diabetes can also be used as a food for diabetics according to the Special Purpose Foods of the Food Standards Code.

The food for diabetics, which belongs to the foods for special medical purposes, is a food prepared/processed with an intention to replace part or all of a diet for patients with limited or impaired ability for normal ingestion, digestion, absorption, or metabolism or persons with nutritional requirements particularly physiologically different from those of normal persons due to diseases or certain clinical conditions.

In order to substitute for part or all of a diet of patients with diabetes, the food for diabetics is required to contain food ingredients and additional nutriments that are composed so that vitamins A, B1, B2, B6, C, D, and E, niacin, folic acid, protein, calcium, iron, and zinc are at least 50% of the nutrient standard values per 1,000 kcal of the food product; the calories derived from saturated fats is less than 10% of the total calories; cholesterol is less than 100 mg per 1,000 kcal of the food product; and calories derived from monosaccharides and disaccharides is less than 10% of the total calories. Accordingly, in order to prepare the food for diabetics, sources of vitamins A, B1, B2, B6, C, D, and E, niacin, folic acid, protein, calcium, iron, and zinc can be further used in addition to the *Schisandra chinensis* fruit water and the bean juice.

The food composition for alleviating diabetes may be soy milk, powdered soy milk, other forms of soy milk, or processed bean curd.

The food composition for alleviating diabetes may be prepared in the form of soy milk containing at least 4 wt. %, preferably 4 to 7 wt. % of soybean solids by adding the

*Schisandra chinensis* fruit water to the bean juice that is a liquid soy milk containing at least 7 wt. % of soybean solids extracted from soybeans.

The food composition for alleviating diabetes may be prepared in other forms of soy milk containing at least 1.4 wt. % of soybean solids by adding the *Schisandra chinensis* fruit water alone or in combination with a saccharified material of grain to the bean juice that is a liquid soy milk containing at least 7 wt. % of soybean solids extracted from soybeans.

The food composition for alleviating diabetes may be prepared in the form of a powdered soy milk containing at least 50 wt. % of soybean solids by using soy milk or other forms of soy milk through a general method, including spray drying, freeze drying, vacuum drying, or hot air drying.

The food composition for alleviating diabetes may be prepared in the form of a pressed bean curd containing at least 30 wt. % of bean curd extracted from soybeans by adding the *Schisandra chinensis* fruit water alone or in combination with a coagulating agent to the bean juice that is a liquid soy milk containing at least 7 wt. % of soybean solids extracted from soybean.

According to ancient literatures such as Donguibogam and Geogapilyong, the *Schisandra chinensis* fruit water is prepared by brewing dried *Schisandra chinensis* fruit overnight in the cooled water previously boiled. Yet, the *Schisandra chinensis* fruit water of the present invention may be a *Schisandra chinensis* fruit juice or a *Schisandra chinensis* fruit extract.

The *Schisandra chinensis* fruit juice may be prepared by soaking fresh *Schisandra chinensis* fruit, thawed *Schisandra chinensis* fruit, refrigerated *Schisandra chinensis* fruit, or dried *Schisandra chinensis* fruit in water, grinding the soaked *Schisandra chinensis* fruit, and filtering out the seeds and debris. It is preferable not to crush the seeds when grinding the *Schisandra chinensis* fruit, because crushed seeds may increase bitter and astringent tastes.

Further, the *Schisandra chinensis* fruit extract is an extract from *Schisandra chinensis* fruit in water, alcohol, or a mixed solvent thereof. In order not to extract bitter and astringent tastes from the *Schisandra chinensis* seeds, it is preferable to perform extraction with water or an aqueous solution of at most 30% (v/v) alcohol at 40° C. or below or extraction from the fruit flesh left after removal of the seeds from the *Schisandra chinensis* fruit.

For example, the *Schisandra chinensis* fruit extract in water may be prepared by extraction with water at 10 to 100° C. for 2 to 48 hours. In order to increase the efficiency of the extraction of water-soluble components with water, the extract may be obtained by extraction in the presence of at least one enzyme selected from cellulase, biscozyme, alcalase, and pectin at 30 to 55° C. for 2 to 24 hours. For example, the extract may be a *Schisandra chinensis* extract in water (i.e., a brew of the *Schisandra chinensis* fruit) prepared by soaking the dried *Schisandra chinensis* fruit at room temperature for 10 to 30 hours, grinding the soaked *Schisandra chinensis* fruit, and filtering out the debris. The *Schisandra chinensis* fruit juice has higher nutritional contents and higher physiological activities and hence better aroma and taste than the brew of the *Schisandra chinensis* fruit.

On the other hand, the extract in alcohol or an aqueous solution of alcohol may be prepared by extraction of *Schisandra chinensis* fruit with a solvent at 20 to 60° C. for 2 to 36 hours, preferably at 40 to 50° C. for 2.5 to 6 hours. Preferably, the extract in an aqueous solution of alcohol has an alcohol content of 0.01 to 50 (v/v) %.

The sugar content of the *Schisandra chinensis* fruit water as measured with a refractometer is 5 to 15° Bx, preferably 7 to 13° Bx, and more preferably 10 to 11° Bx. Hereinafter, the content of the *Schisandra chinensis* fruit water is reduced based on the *Schisandra chinensis* fruit water that measures 10° Bx. Further, the pH of the *Schisandra chinensis* fruit water is 4.5 to 5.5, preferably 4.7 to 5.3.

The bean juice is a liquid soy milk prepared by steaming and grinding soybeans and then filtering out bean pulps. In the preparation, the soybeans may be peeled and steamed so that they can be softened by enzyme deactivation. Prior to the steaming process, the soybeans may be soaked in water for 8 to 16 hours. While grinding the steamed soybeans in the presence of water, a small amount of a defoaming agent may be added to reduce the generation of foam, and under necessity, sodium hydroxide or the like may be used to neutralize the liquid product of the grinding process. Further, a centrifugal separation may be carried out to remove bean pulps, and under necessity, the liquid soy milk removed of bean pulps may be homogenized under 100 to 250 bar with a homogenizer. Hereinafter, the content of the bean juice is reduced based on the liquid soy milk containing 7 wt. % of soybean solids.

The *Schisandra chinensis* fruit water and the bean juice are mixed together at a weight ratio of 1:0.1~4, preferably 1:0.8~3, and more preferably 1:1.3~2. When the content of the bean juice relative to the *Schisandra chinensis* fruit water is less than the lower limit, a strong sour taste is created due to a relatively large amount of the *Schisandra chinensis* fruit water and the proteins of the bean juice is denatured to produce a lump of curds like soft tofu, which may not be good for the alleviation of diabetes. When the content of the bean juice relative to the *Schisandra chinensis* fruit water exceeds the upper limit, it may create a thick taste and deteriorate the overall sensory properties and the diabetes-alleviating effect as well.

The food composition for alleviating diabetes may further include a saccharified material of grain. The saccharified material of grain may be prepared by saccharifying at least one grain selected from rice, wheat, and barley, preferably rice, such as polished rice, unpolished (brown) rice, or glutinous rice, and more preferably polished rice.

The saccharified material of grain is a powder prepared by mixing the grain with malt or a saccharifying enzyme to saccharify the grain and then drying the saccharified grain.

The saccharifying enzyme is glucoamylase, α-amylase, or a mixture of these enzymes. The glucoamylase is an enzyme having a starch-liquefaction activity or a dextrogenic activity, and the α-amylase is an enzyme having a saccharogenic activity. Yet, any enzyme available for saccharification of starch can be used without limitation. The glucoamylase may be derived from a *Bacillus* sp. strain, and the α-amylase may be derived from an *Aspergillus* sp. strain.

The saccharified material of grain may be prepared through an enzymatic reaction, for example, by mixing 20 to 50 parts by weight, preferably 30 to 40 parts by weight of a grain flour with 100 parts by weight of water to prepare a grain suspension and adding 0.005 to 0.5 part by weight, preferably 0.01 to 0.1 part by weight of glucoamylase and 0.005 to 0.5 part by weight, preferably 0.01 to 0.1 part by weight of α-amylase with respect to 100 parts by weight of the grain suspension. Alternatively, the saccharified material of grain may be prepared through an enzymatic reaction by mixing the grain with malt flour in place of the saccharifying enzyme at a weight ratio of 1:0.1~5.

The enzymatic reaction may be performed until 60 to 95 wt. %, preferably 70 to 90 wt. %, and more preferably 75 to 85 wt. % of the carbohydrates contained in the rice suspension is converted into glucose.

For this, the enzymatic reaction may be carried out at 55 to 75° C., preferably 60 to 65° C. for 2 to 8 hours, preferably 3 to 7 hours, and more preferably 4 to 5 hours. As the enzymatic reaction occurs within the defined temperature and time ranges, the starch of the grain flour contained in the grain suspension is decomposed into dextrin and glucose to increase the sweetness. If the temperature and the time for the enzymatic reaction are above the defined temperature and time ranges, the glucose content is raised to increase the sweetness, but the *Schisandra chinensis* fruit water has an insignificant effect of improving properties and fails to inhibit coagulation of the bean juice.

An enzyme deactivation step may be further included to deactivate the enzyme so that the enzymatic reaction is suspended after its completion in the saccharification step. The process of enzyme deactivation may be applied by a method known in the related art without limitation; for example, by heating at 80 to 90° C. for 5 to 30 minutes and then cooling down to 20 to 40° C.

The saccharified rice gruel prepared in the above step may have a pH value of 5.5 to 6.5, a glucose content of 8 to 15 wt. %, preferably 10 to 13 wt. %, and a sugar content of 6 to 20° Bx, preferably 8 to 15° Bx.

The *Schisandra chinensis* fruit water, the bean juice, and the saccharified material of grain are mixed at a weight ratio of 1:0.1~4:0.1~3, preferably 1:0.8~3:0.2~1.5, and more preferably 1:1.3~2:0.2~1.5. When the content of the saccharified material of grain with respect to the *Schisandra chinensis* fruit water is less than the lower limit, the sweet taste is week and the bean juice possibly coagulates due to the *Schisandra chinensis* fruit water, resulting in giving an insignificant effect of alleviating diabetes. When the content of the saccharified material of grain with respect to the *Schisandra chinensis* fruit water exceeds the upper limit, it may increase the viscosity relative to that of soy milk drinks, create a thick taste, deteriorate the overall sensory properties, and result in no effect of alleviating diabetes.

In order to deliver a sweet taste, increase the acceptability and make the effect of alleviating diabetes, the food composition for alleviating diabetes may further include at least one sweetener selected from aspartame, acesulfame calcium, sorbitol, trehalose, palatinose, tagatose, xylitol, and oligosaccharide. The sweetener may be used in an amount of 0.0001 to 10 parts by weight, preferably 0.001 to 5 parts by weight with respect to 100 parts by weight of the bean juice.

The present invention also provides a method for preparing a food composition for alleviating diabetes.

The method for preparing a food composition for alleviating diabetes may include: (1) extracting juice from *Schisandra chinensis* fruit or obtaining an extract of *Schisandra chinensis* fruit in water, alcohol, or a mixed solvent thereof to prepare a *Schisandra chinensis* fruit water; (2) steaming and grinding beans and then filtering out bean pulps to obtain a bean juice with bean pulps removed; and (3) mixing the *Schisandra chinensis* fruit water and the bean juice.

The method for preparing a food composition for alleviating diabetes may further include: mixing a grain with malt or a saccharifying enzyme to saccharify the grain and then drying the saccharified grain to obtain a saccharified material of grain. The saccharified material of grain may be added in the mixing step.

The expression "containing/comprising as an active ingredient" as used herein refers to including the *Schisandra chinensis* fruit water and the bean juice, or the *Schisandra chinensis* fruit water, the bean juice and the saccharified material of grain in amounts enough to acquire the efficacies or activities of the present invention. The *Schisandra chinensis* fruit water, the bean juice and/or the saccharified material of grain are all natural materials and hence have no side effects to the human body even if used in excessive amounts. It is therefore possible for those skilled in the art to select the upper limit of the quantity of the *Schisandra chinensis* fruit water, the bean juice and/or the saccharified material of grain contained in the composition of the present invention within an appropriate range.

The food composition for alleviating diabetes according to the present invention may be used as an additive to a variety of foods. The foods to which the composition of the present invention is applicable may include, for example, beverages, alcoholic drinks, confectionery, diet bars, dairy products, meats, chocolates, pizzas, ramen, other noodles, gums, ice creams, vitamin complexes, health supplements, and so forth.

The food composition for alleviating diabetes according to the present invention may include ingredients commonly used in the food production, such as proteins, carbohydrates, fats, nutrients, seasonings, and flavoring agents. The examples of the carbohydrates may include monosaccharides, such as glucose and fructose; disaccharides, such as maltose, sucrose, and oligosaccharides; and polysaccharides, such as regular sugars (e.g., dextrin and cyclodextrin) and sugar alcohols (e.g., xylitol, sorbitol, and erythritol). The flavoring agents may include natural flavoring agents, such as taumatin or *stevia* (e.g., rebaudioside glycyrrhizin), and synthetic flavoring agents, such as saccharin or aspartame. When used in the preparation of drinks or beverages, for example, the food composition of the present invention may further include citric acid, liquid fructose, sugar, glucose, acetic acid, malic acid, fruit juice, or various plant extracts.

In the health functional food of the present invention, the contents of the *Schisandra chinensis* fruit water and the bean juice, or those of the *Schisandra chinensis* fruit water, the bean juice and the saccharified material of grain are dependent upon the type of the health functional food and thus cannot be defined across the board, but within the range that does not harm the original taste of the food; typically 0.01 to 100 wt. %, preferably 0.1 to 50 wt. % with respect to the food. In the case of the health functional foods in the form of pills, granules, tablets, or capsules, the *Schisandra chinensis* fruit water and the bean juice, or the *Schisandra chinensis* fruit water, the bean juice and the saccharified material of grain may be used normally in the amount range of 0.1 to 50 wt. %, preferably 0.5 to 30 wt. %.

The present invention is also directed to the use of a complex of a *Schisandra chinensis* fruit water and a bean juice for preparation of a food for alleviating diabetes.

Hereinafter, the disclosure of the present invention will be described with reference to the preferred embodiments. It is apparent to those skilled in the art that the preferred embodiments are given for the understanding of the disclosure of the present invention and susceptible to various changes and modifications within the scope and technical spirit of the present invention. Such changes and modifications are, of course, included in the claims of the present invention.

Preparation Example 1: Preparation of Juice from Fresh *Schisandra Chinensis* Fruits Washed fresh *Schisandra chinensis* fruits were blended with a mixer and removed of seeds and debris by filtration through a 70-mesh filter cloth to obtain a juice from fresh *Schisandra chinensis* fruits. The juice had a pH value of 5.0 and a sugar content of 10° Bx.

Preparation Example 2: Preparation of Juice from Dried *Schisandra Chinensis* Fruits Dried *Schisandra chinensis* fruits having a moisture content of 8 wt. % were mixed with water at a weight ratio of 1:18 and soaked at the room temperature for 24 hours. The soaked *Schisandra chinensis* fruits were blended with a mixer and removed of seeds and debris by filtration through a 70-mesh filter cloth to obtain a juice from dried *Schisandra chinensis* fruits. The juice had a pH value of 4.7 and a sugar content of 10° Bx.

Preparation Example 3: Preparation of Bean Juice

Washed soybeans were immerged in water and soaked for 12 hours. The soaked soybeans were steamed at 110° C. and then rinsed with cold water to remove skins. The peeled soybeans were blended with a mixer and filtered through a 70-mesh filter cloth to obtain a bean juice with bean pulps removed. The bean juice contained 7 wt. % of soybean solids.

Preparation Example 4: Preparation of Saccharified Rice Meal 200 g of gelatinized rice flour and 2 g of malt flour were mixed with water to have the total volume of 1000 ml. The mixture was subjected to saccharification at 65° C. for 4 hours, heated up to 85° C. for 20 hours to deactivate enzymes, cooled down, and then freeze-dried into a saccharified rice meal. The saccharified rice meal thus obtained had a pH value of 6.0, a glucose content of 12 wt. %, and a sugar content of 13° Bx. For use in the following examples, the saccharified rice meal was pre-diluted with water of which the weight was three times the weight of the saccharified rice meal.

Example 1: Juice of Fresh *Schisandra Chinensis* Fruits+Bean Juice+Saccharified Material of Grain The juice of fresh *Schisandra chinensis* fruits of Preparation Example 1, the bean juice of Preparation Example 3, and the dilution of the saccharified rice meal of Preparation Example 4 were mixed at a weight ratio of 1:1:1 to obtain a food composition for alleviating diabetes according to Example 1.

Example 2: Juice of Fresh *Schisandra Chinensis* Fruits+Bean Juice+Saccharified Material of Grain The juice of fresh *Schisandra chinensis* fruits of Preparation Example 1, the bean juice of Preparation Example 3, and the dilution of the saccharified rice meal of Preparation Example 4 were mixed at a weight ratio of 1:0.6:0.6 to obtain a food composition for alleviating diabetes according to Example 2.

Example 3: Juice of Fresh *Schisandra Chinensis* Fruits+Bean Juice+Saccharified Material of Grain The juice of fresh *Schisandra chinensis* fruits of Preparation Example 1, the bean juice of Preparation Example 3, and the dilution of the saccharified rice meal of Preparation Example 4 were mixed at a weight ratio of 1:0.5:0.5 to obtain a food composition for alleviating diabetes according to Example 3.

Example 4: Juice of Fresh *Schisandra Chinensis* Fruits+Bean Juice+Saccharified Material of Grain The juice of fresh *Schisandra chinensis* fruits of Preparation Example 1, the bean juice of Preparation Example 3, and the dilution of the saccharified rice meal of Preparation Example 4 were mixed at a weight ratio of 1:0.33:0.33 to obtain a food composition for alleviating diabetes according to Example 4.

Example 5: Juice of Fresh *Schisandra Chinensis* Fruits+Bean Juice+Saccharified Material of Grain The juice of fresh *Schisandra chinensis* fruits of Preparation Example 1, the bean juice of Preparation Example 3, and the dilution of the saccharified rice meal of Preparation Example 4 were mixed at a weight ratio of 1:1.5:1 to obtain a food composition for alleviating diabetes according to Example 5.

Example 6: Juice of Dried *Schisandra Chinensis* Fruits+Bean Juice+Saccharified Material of Grain The juice of dried *Schisandra chinensis* fruits of Preparation Example 2, the bean juice of Preparation Example 3, and the dilution of the saccharified rice meal of Preparation Example 4 were mixed at a weight ratio of 1:0.6:0.6 to obtain a food composition for alleviating diabetes according to Example 6.

Example 7: Juice of Dried *Schisandra Chinensis* Fruits+Bean Juice+Sugar

The juice of dried *Schisandra chinensis* fruits of Preparation Example 2, the bean juice of Preparation Example 3, and sugar water prepared by dissolving sugar in water of which the weight was three times the weight of the sugar were mixed at a weight ratio of 1:1:1 to obtain a food composition for alleviating diabetes according to Example 7.

Example 8: Juice of Dried *Schisandra Chinensis* Fruits+Bean Juice+Honey

The juice of dried *Schisandra chinensis* fruits of Preparation Example 2, the bean juice of Preparation Example 3, and honey were mixed at a weight ratio of 1:1:1 to obtain a food composition for alleviating diabetes according to Example 8.

Example 9: Juice of Dried *Schisandra Chinensis* Fruits+Bean Juice+Honey

The juice of dried *Schisandra chinensis* fruits of Preparation Example 2, the bean juice of Preparation Example 3, and honey were mixed at a weight ratio of 1:2:1 to obtain a food composition for alleviating diabetes according to Example 9.

Example 10: Juice of Dried *Schisandra Chinensis* Fruits+Bean Juice+Saccharified Material of Grain The juice of dried *Schisandra chinensis* fruits of Preparation Example 2, the bean juice of Preparation Example 3, and the dilution of the saccharified rice meal of Preparation Example 4 were mixed at a weight ratio of 1:2:1 to obtain a food composition for alleviating diabetes according to Example 10.

Example 11: Juice of Dried *Schisandra Chinensis* Fruits+Bean Juice+Saccharified Material of Grain The juice of dried *Schisandra chinensis* fruits of Preparation Example 2, the bean juice of Preparation Example 3, and the dilution of the saccharified rice meal of Preparation Example 4 were mixed at a weight ratio of 1:1:1 to obtain a food composition for alleviating diabetes according to Example 11.

Comparative Example 1: Juice of Fresh *Schisandra Chinensis* Fruits Alone

The juice of fresh *Schisandra chinensis* fruits according to Preparation Example 1 was used alone.

Comparative Example 2: Bean Juice Alone

The bean juice of Preparation Example 3 was used alone.

Comparative Example 3: Juice of Fresh *Schisandra Chinensis* Fruits+Bean Extract+Saccharified Material of Grain The procedures were performed in the same manner as described in Example 1, excepting that a soybean extract in hot water was used while the juice of fresh *Schisandra chinensis* fruits, the bean extract, and the dilution of the saccharified rice meal were mixed at a weight ratio of 1:0.6:0.6 to obtain a food composition for alleviating diabetes according to Comparative Example 3.

Comparative Example 4: Commercial Soy Milk

The soy milk product commercially available with the highest market share was used alone as the Comparative Example 4.

Experimental Example 1: Coagulation and Viscosity of Bean Juice

The food compositions for diabetics according to Examples 1, 8, 9, 10, and 11 were measured in regards to the viscosity depending on the mixing ratio of the *Schisandra chinensis* fruit water and the bean juice and the presence of the saccharified rice meal in the step of mixing the *Schisandra chinensis* fruit water and the bean juice. The measurement results were presented in Table 1. Further, the coagulation of the bean juice was checked by the time intervals, and the results were shown in FIG. 1.

TABLE 1

| Div. | Omisu: Bean juice (weight ratio) | Presence of Saccharified rice meal | Viscosity |
|---|---|---|---|
| Example 1 | 1:1 | O | 0.03284 |
| Example 8 | 1:1 | X | 0.01550 |
| Example 9 | 1:2 | X | 0.00970 |
| Example 10 | 1:2 | O | 0.01735 |
| Example 11 | 1:1 | O | 0.03782 |
| Comparative Example 4 | — | — | 0.00824 |

Referring to Table 1, the viscosity increased with an increase in the weight proportion of the *Schisandra chinensis* fruit water (Omisu), provided that the other conditions were the same; the food composition using the juice of fresh *Schisandra chinensis* fruits had a higher viscosity than those using the juice of dried *Schisandra chinensis* fruits, provided that the other conditions were the same; and the food compositions using the saccharified rice meal had a higher viscosity than those using honey, provided that the other conditions were the same. In addition, the food compositions of Examples 8, 9 and 10 were similar to the commercial soy milk in regards to the viscosity and the body feel in terms of sensory properties associated with drinking properties.

Although being prepared by mixing the ingredients at 200 rpm for about 10 minutes without a homogenization process using a high-speed agitator and a homogenizer as normally used in the preparation process for bean juice of the Preparation Example 3 or the mixing process of the Examples, the food compositions of the Examples 1, 10 and 11 using a saccharified rice meal had no coagulation caused by the addition of the *Schisandra chinensis* fruit water (Omisu) and started to form a little phase separation on the supernatant in 2 hours after the preparation. It was therefore apparent that the food compositions containing a saccharified gain meal can be prepared in the form of a beverage such as soy milk or other forms of soy milk even though the *Schisandra chinensis* fruit water was used in the same amount of the bean juice.

In the Examples 8 and 9 not using a saccharified material of grain and the Example 8 using the *Schisandra chinensis* fruit water in the same amount of the bean juice, the proteins of the bean juice started to coagulate in 30 minutes after the preparation, so the food compositions were more suitable for preparation of foods such as a powdered soy milk or a pudding-like processed tofu rather than soy milk or other forms of soy milk.

In the Example 9 having a low content of the *Schisandra chinensis* fruit water and using no saccharified material of grain, the bean juice did not coagulate so severely as in the Example 8 but started to coagulate gradually in 2 hours after the preparation. It was therefore considered preferable to add a stabilizing agent typically available for foods in order to prevent the coagulation of the bean juice in the case of preparing a beverage such as soy milk or other forms of soy milk without using a saccharified rice meal. Yet, it was expected to reduce the coagulation of the bean juice remarkably by additionally using a high-speed agitation or homogenization process.

Experimental Example 2: In-Vitro Enzyme Activity: Inhibitory Activity Against α-Glucosidase In the α-glucosidase inhibition assay, the measurement method of Tibbot and Skadsen (1996) was employed using α-glucosidase (Sigma, USA) derived from a yeast as an enzyme and p-nitrophenyl-α-D-glucopyranoside (Sigma, USA) as a substrate. The α-glucosidase was dissolved in a 100 mM phosphate buffer (pH 7.0) containing 0.2% BSA and 0.02% $NaN_3$ to prepare a 0.7-unit enzyme solution. The p-nitrophenyl-α-D-glucopyranoside was dissolved in a 100 mM phosphate buffer (pH 7.0) to prepare a 10 mM substrate solution. Subsequently, 50 μl of each sample was added into a microplate, and 100 μl of the α-glucosidase enzyme was added. Then, incubation was conducted at the room temperature (25° C.) for 5 minutes and the absorbance at 405 nm was measured with a multi detection reader (Infinite 200, TECAN Group Ltd., Switzerland). 50 μl of the substrate solution was added, and after 2 minutes, the absorbance at 405 nm was measured with the multi detection reader to determine the enzyme inhibition rate.

% Inhibition=[(A0−A1)/A0]×100    [Equation 1]

where A0 is the absorbance of the control; and A1 is the absorbance of test samples.

TABLE 2

| Div. | Concentration (ug/ml) | | | | |
|---|---|---|---|---|---|
| (Unit: %) | 0 | 10 | 100 | 1000 | 10000 |
| Example 1 | 0.0 | 0.6 | 5.7 | 13.1 | 24.4 |
| Example 2 | 0.0 | 1.1 | 4.8 | 13.4 | 23.6 |
| Example 3 | 0.0 | 1.8 | 4.5 | 10.2 | 21.4 |
| Example 4 | 0.0 | 0.0 | 3.8 | 11.5 | 19.1 |
| Example 5 | 0.0 | 1.5 | 7.9 | 15.2 | 27.2 |
| Example 6 | 0.0 | 0.4 | 1.3 | 7.1 | 19.8 |
| Example 7 | 0.0 | 0.5 | 1.7 | 7.5 | 18.9 |
| Example 8 | 0.0 | 0.4 | 1.9 | 7.5 | 18.0 |
| Comparative Example 1 | 0.0 | 0.5 | 2.0 | 4.3 | 9.7 |
| Comparative Example 2 | 0.0 | −0.5 | 3.6 | 7.0 | 10.7 |
| Comparative Example 3 | 0.0 | 0.4 | 1.8 | 4.9 | 9.8 |

Test animals, ICR mice (6 weeks old, male) were purchased from Samtaco Bio Korea (Gyeonggi, South Korea) and used for experiments after a one-week acclimatization period. For the experimental diet, the test animals had free access to regular solid food (Samtaco, Gyeonggi, South Korea) and filtered drinking water that was daily changed drinking water. During the breeding period, the breeding conditions were maintained to have temperature 23±1° C., humidity 50±5%, noise 60 phone or less, lighting time 23 hours per day (08:00~20:00), illumination 150 to 300 Lux, and 10 to 12 times of ventilation per hour.

2-1. Oral Glucose Tolerance Test (OGTT)

The test animals that fasted for more than 8 hours were measured in regards to the fasting blood glucose in the caudal vein with a blood glucose meter (Autocheck, Diatech Korea Co., Ltd.), randomly arranged by the group according to the egg mass method, and then fed with each sample (100 mg/kg) by means of oral administration. After 30 minutes, the blood glucose was measured again, and glucose as a blood-glucose-increasing factor was orally administered to each group with a dose of 2 g/kg according to the experimental method. Then, the blood glucose was measured in the caudal vein for up to 120 minutes at 30-minute intervals. The control group was a non-administration group.

TABLE 3

| Div. | Time (min) | | | | | |
|---|---|---|---|---|---|---|
| | −30 | 0 | 30 | 60 | 90 | 120 |
| Control | 88.14 ± 10.85 | 126.29 ± 18.35 | 435.57 ± 46.12 | 299.29 ± 46.78 | 153.00 ± 20.89 | 110.14 ± 14.42 |
| Example 1 | 86.29 ± 10.14 | 125.71 ± 10.49 | 380.29 ± 44.98 | 217.29 ± 32.46 | 137.29 ± 17.28 | 106.00 ± 13.62 |
| Example 2 | 85.33 ± 11.13 | 120.72 ± 9.17 | 374.23 ± 40.12 | 213.13 ± 30.11 | 140.12 ± 18.12 | 109.33 ± 11.27 |
| Example 3 | 84.17 ± 8.89 | 122.94 ± 10.12 | 354.73 ± 38.22 | 212.36 ± 35.35 | 145.21 ± 10.88 | 118.65 ± 11.23 |
| Example 4 | 86.42 ± 6.33 | 130.25 ± 3.27 | 355.75 ± 41.18 | 222.34 ± 38.45 | 149.87 ± 11.92 | 128.22 ± 12.21 |
| Example 5 | 85.57 ± 7.66 | 111.14 ± 3.67 | 345.29 ± 37.90 | 218.00 ± 35.22 | 135.29 ± 12.98 | 103.29 ± 15.85 |
| Example 6 | 88.82 ± 8.45 | 121.67 ± 8.38 | 365.00 ± 40.74 | 232.00 ± 38.55 | 144.87 ± 10.26 | 118.12 ± 13.44 |
| Example 7 | 89.57 ± 8.02 | 126.57 ± 9.38 | 396.86 ± 43.08 | 236.29 ± 31.14 | 159.00 ± 22.89 | 120.57 ± 10.72 |
| Example 8 | 88.51 ± 7.48 | 127.68 ± 10.42 | 390.38 ± 40.38 | 230.02 ± 33.02 | 150.77 ± 21.63 | 123.33 ± 8.09 |
| Comparative Example 1 | 93.14 ± 8.93 | 140.86 ± 15.43 | 390.29 ± 26.70 | 226.86 ± 27.42 | 154.86 ± 9.56 | 130.43 ± 20.40 |
| Comparative Example 2 | 85.57 ± 7.46 | 135.86 ± 14.23 | 395.71 ± 53.22 | 247.14 ± 35.86 | 167.57 ± 16.47 | 132.86 ± 16.10 |
| Comparative Example 3 | 85.34 ± 7.66 | 137.32 ± 9.22 | 392.27 ± 40.12 | 245.17 ± 35.28 | 158.85 ± 20.17 | 131.38 ± 10.33 |

As can be seen from Table 2, the food compositions prepared according to the Examples 1 to 8 of the present invention displayed a high inhibitory activity against α-glucosidase in a concentration-dependent manner relative to those of the Comparative Examples 1, 2 and 3. Particularly, the food composition of the Example 1 using a juice of fresh *Schisandra chinensis* fruits had a higher inhibitory activity against α-glucosidase than that of the Example 6 using an extract of *Schisandra chinensis* fruits in water; and the food composition of the Example 1 using a bean juice was far superior in the inhibitory activity against α-glucosidase to that of the Comparative Example 3 using a bean extract.

Experimental Example 3: In-vitro Animal Testing

Test Animals

As can be seen from Table 3, the food compositions prepared according to the Examples 1 to 8 of the present invention had a higher anti-hyperglycemic activity than those of the Comparative Examples 1, 2 and 3. In particular, the food compositions of the Examples 1, 2, 3, and 5 displayed a higher anti-hyperglycemic activity than the non-administration control group and the other groups.

2-2. $AUG_{0-2h}$ Measurement

After the measurement of the blood glucose in 2-1, the area under the blood glucose curve was calculated to analyze the change in the blood glucose for each test group. The control group was a non-administration group.

TABLE 4

| Div. | AUC (hours A mg/dL) |
|---|---|
| Control | 33520.8 ± 4600.3$^c$ |
| Example 1 | 29069.2 ± 2881.4$^a$ |
| Example 2 | 29241.9 ± 2527.6$^{ab}$ |
| Example 3 | 29551.5 ± 2109.7$^b$ |
| Example 4 | 29848.1 ± 1895.4$^b$ |
| Example 5 | 28849.1 ± 3449.3$^a$ |
| Example 6 | 31015.3 ± 2451.0$^b$ |
| Example 7 | 31994.1 ± 2961.4$^{bc}$ |
| Example 8 | 31788.5 ± 2856.1$^{bc}$ |
| Comparative Example 1 | 32225.0 ± 2187.4$^c$ |
| Comparative Example 2 | 32754.4 ± 3234.0$^c$ |
| Comparative Example 3 | 32047.4 ± 1945.5$^c$ |

As can be seen from Table 4, the food compositions prepared according to the Examples 1 to 8 of the present invention had lower AUG values than those of the Comparative Examples 1, 2 and 3. In other words, the food compositions of the Examples 1 to 6 displayed a high anti-hyperglycemic activity after meals.

Experimental Example 4: Measurement of Marker Components

In the isolation and quantitative analysis of 12 marker components, including six lignin components in the Schisandra chinensis fruits (i.e., gomisin A, gomisin C, schisandrin, γ-schisandrin, deoxyschisandrin, and schisandrin C) and six isoflavone components in beans (i.e., daidzin, glycitin, genistin, daidzein, glycitein, and genistein), the UPLC-MS/MS system using ultrahigh-performance liquid chromatography (HSS T3 column 2.1×100 mm, 1.8 μm; waters) associated with Waters Xevo TQ triple-quadrupole (Waters, Miliford, MA, USA) was used for quantitative determination. For chromatographic isolation, a moving phase consisting of 0.1% formic acid in water and acetonitrile was used for a concentration-based gradient elution of analytes for 10 minutes at a flow rate of 0.5 mL/min. The isolated substances were detected with LC-MS/MS. The multiple reaction monitoring (MRM) mode was adopted as an ESI positive mode of the LC-MS/MS system. The capillary and sampling cone voltages were set to 3.3 kV and 36 V, respectively. The collision energy was 23 kV. The desolvation flow rate was 800 L/h at 400° C., and the temperature of the source was 150° C. All the information of the MS data was extracted with Marker Lynx (Waters) installed in the equipment.

TABLE 5

| | Div. | Examples 1 | 2 | 3 | 4 | 5 | 6 |
|---|---|---|---|---|---|---|---|
| ligana (mg/g) | deoxy-schisandrin | 0.11 ± 0.01 | 0.13 ± 0.01 | 0.16 ± 0.00 | 0.17 ± 0.01 | 0.11 ± 0.01 | 0.10 ± 0.01 |
| | gomisin A | 0.12 ± 0.00 | 0.17 ± 0.00 | 0.21 ± 0.01 | 0.27 ± 0.00 | 0.14 ± 0.00 | 0.11 ± 0.00 |
| | r-schisandrin | 0.12 ± 0.01 | 0.13 ± 0.00 | 0.14 ± 0.00 | 0.13 ± 0.01 | 0.11 ± 0.01 | 0.12 ± 0.00 |
| | gomisin C | 0.02 ± 0.0 | 0.03 ± 0.00 | 0.04 ± 0.00 | 0.05 ± 0.00 | 0.03 ± 0.00 | 0.02 ± 0.01 |
| | schizandrol A | 0.32 ± 0.00 | 0.42 ± 0.00 | 0.51 ± 0.00 | 0.62 ± 0.00 | 0.34 ± 0.00 | 0.33 ± 0.00 |
| | schisandrin C | 0.08 ± 0.00 | 0.09 ± 0.00 | 0.10 ± 0.01 | 0.09 ± 0.01 | 0.07 ± 0.01 | 0.05 ± 0.00 |
| | Total content | 0.78 | 0.97 | 1.17 | 1.33 | 0.79 | 0.73 |
| isoflavone (ug/g) | daidzein | 9.33 ± 1.15 | 6.67 ± 1.15 | 6.67 ± 1.15 | 8.00 ± 0.00 | 11.33 ± 1.15 | 10.67 ± 0.98 |
| | genistein | 6.00 ± 0.00 | 4.00 ± 0.00 | 4.00 ± 0.00 | 4.67 ± 1.15 | 8.00 ± 0.00 | 6.00 ± 1.15 |
| | glycitein | — | — | — | — | — | — |
| | daidzin | 54.67 ± 2.31 | 51.33 ± 1.15 | 55.33 ± 3.06 | 56.67 ± 3.06 | 88.0 ± 1.11 | 58.67 ± 1.06 |
| | genistin | 50.67 ± 3.06 | 4 6.67 ± 1.15 | 48.0 ± 0.00 | 46.0 ± 2.00 | 76.67 ± 1.15 | 54.57 ± 2.00 |
| | glycitin | 18.0 ± 2.00 | 14.67 ± 1.15 | 16.67 ± 1.15 | 16.67 ± 1.15 | 26.0 ± 2.00 | 19.0 ± 1.15 |
| | Total content | 138.67 | 123.33 | 130.67 | 132.00 | 210.00 | 148.91 |

| | Div. | Examples 7 | 8 | Comparative Examples 1 | 2 | 3 |
|---|---|---|---|---|---|---|
| ligana (mg/g) | deoxy-schisandrin | 0.05 ± 0.01 | 0.04 ± 0.00 | 0.26 ± 0.03 | — | 0.04 ± 0.00 |
| | gomisin A | 0.05 ± 0.00 | 0.04 ± 0.00 | 0.46 ± 0.01 | — | 0.05 ± 0.01 |
| | r-schisandrin | 0.08 ± 0.02 | 0.09 ± 0.01 | 0.13 ± 0.02 | — | 0.07 ± 0.00 |
| | gomisin C | 0.04 ± 0.00 | 0.06 ± 0.00 | 0.09 ± 0.01 | — | 0.04 ± 0.01 |
| | schizandrol A | 0.16 ± 0.01 | 0.14 ± 0.01 | 0.93 ± 0.02 | — | 0.15 ± 0.00 |
| | schisandrin C | 0.05 ± 0.01 | 0.04 ± 0.01 | 0.11 ± 0.02 | — | 0.04 ± 0.00 |
| | Total content | 0.43 | 0.41 | 1.98 | — | 0.38 |
| isoflavone (ug/g) | daidzein | 5.33 ± 1.15 | 5.15 ± 1.15 | — | 34.67 ± 3.06 | 4.12 ± 0.05 |
| | genistein | 4.00 ± 0.00 | 3.88 ± 0.00 | — | 28.0 ± 0.00 | 3.45 ± 1.15 |
| | glycitein | — | — | — | 2.000.00 | — |
| | daidzin | 56.67 ± 2.31 | 57.15 ± 2.85 | — | 301.33 ± 7.57 | 44.17 ± 2.31 |
| | genistin | 52.00 ± 2.00 | 53.01 ± 2.00 | — | 212.67 ± 6.43 | 40.65 ± 1.15 |
| | glycitin | 17.33 ± 1.15 | 17.85 ± 3.06 | — | 107.33 ± 4.16 | 11.48 ± 2.00 |
| | Total | 135.33 | 137.04 | — | 686.00 | 103.87 |

TABLE 5-continued content

As can be seen from Table 5, all the food composition prepared according to the Examples 1 to 8 had high lignin and isoflavone contents.

In contrast, the food composition of the Comparative Example contained none of the isoflavone components; that of the Comparative Example 2 contained none of the lignin components; and that of the Comparative Example 3 had lower lignin and isoflavone contents than those of every Example.

Experimental Example 5: Sensory Evaluation 20 panel volunteers were asked to consume the compositions prepared in Examples and Comparative Examples and participate in the sensory evaluations using the 9-point hedonic scale to obtain mean liking scores as presented in Table 6.

Colour, taste, aroma, and overall acceptability:
1 point=Dislike extremely, 9 points=Like extremely

TABLE 6

| Div. | Colour | Taste | Aroma | Overall acceptability |
|---|---|---|---|---|
| Example 1 | 7.3 | 7.5 | 7.0 | 7.0 |
| Example 2 | 8.0 | 8.1 | 7.8 | 8.0 |
| Example 3 | 7.7 | 7.9 | 7.4 | 7.7 |
| Example 4 | 7.5 | 7.4 | 7.0 | 7.2 |
| Example 5 | 7.9 | 7.9 | 8.0 | 7.8 |
| Example 6 | 6.8 | 6.2 | 6.5 | 6.7 |
| Example 7 | 6.1 | 6.5 | 6.8 | 6.4 |
| Example 8 | 6.5 | 6.0 | 6.9 | 6.7 |
| Comparative Example 1 | 4.2 | 4.4 | 5.1 | 4.3 |
| Comparative Example 2 | 3.0 | 2.9 | 3.1 | 2.8 |
| Comparative Example 3 | 3.5 | 4.7 | 4.3 | 4.5 |

As can be seen from Table 6, the food compositions prepared according to the Examples 1 to 8 were all excellent in colour, taste, aroma, and overall acceptability relative to those of the Comparative Examples 1, 2 and 3.

Hereinafter, a description will be given as to examples of the formulation of the composition containing the powder of the present invention, which examples are provided for illustration of the present invention and not construed to limit the present invention.

Formulation Example 1. Preparation of Functional Soy Milk

| | |
|---|---|
| Mixture of Example 1 | 900 mL |
| Vitamin C | 100 mg |
| Mineral mixture | 10 mg |

We claim:

1. A method for treating or preventing blood sugar control disorder or diabetes in a subject in need thereof, administrating a beverage composition comprising a *Schisandra chinensis* fruit water, a bean juice and a saccharified material of grain powder as active ingredients,
wherein the *Schisandra chinensis* fruit water is a *Schisandra chinensis* fruit juice or a *Schisandra chinensis* fruit extract,
wherein the *Schisandra chinensis* fruit extract is an extract in water, alcohol, or a mixed solvent thereof,
wherein the beverage composition is a health functional food for blood sugar control or a food for diabetics,
wherein the beverage composition is soy milk or powdered soy milk,
wherein the saccharified material of grain powder is a powder prepared by mixing 20 to 50 parts by weight of a grain flour with 100 parts by weight of water, adding malt or a saccharifying enzyme to saccharify the grain flour, and then drying the saccharified grain flour,
wherein the *Schisandra chinensis* fruit water, the bean juice, and the saccharified grain powder are mixed at a weight ratio of 1:0.8~2:0.2~1.5.

2. The method according to claim 1, wherein the bean juice is a liquid soy milk containing at least 7 wt. % of soybean solids extracted from soybeans.

3. The method according to claim 1, wherein the saccharified material of grain powder is prepared by saccharifying at least one grain selected from rice, wheat, and barley.

4. The method according to claim 1, further comprising at least one sweetener selected from the group consisting of aspartame, acesulfame calcium, sorbitol, trehalose, palatinose, tagatose, xylitol, and oligosaccharide.

* * * * *